(12) United States Patent
Matsumoto et al.

(10) Patent No.: US 8,912,117 B2
(45) Date of Patent: Dec. 16, 2014

(54) CELLULOSE GEL FOR PURIFICATION OF IMMUNOGLOBULIN

(75) Inventors: Yoshihiro Matsumoto, Minamata (JP); Yasuto Umeda, Minamata (JP); Shigeyuki Aoyama, Minamata (JP); Masami Todokoro, Yokohama (JP)

(73) Assignee: JNC Corporation, Tokyo (JP)

( * ) Notice: Subject to any disclaimer, the term of this patent is extended or adjusted under 35 U.S.C. 154(b) by 455 days.

(21) Appl. No.: 13/201,647

(22) PCT Filed: Feb. 18, 2010

(86) PCT No.: PCT/JP2010/052407
§ 371 (c)(1),
(2), (4) Date: Aug. 16, 2011

(87) PCT Pub. No.: WO2010/095673
PCT Pub. Date: Aug. 26, 2010

(65) Prior Publication Data
US 2011/0301330 A1    Dec. 8, 2011

(30) Foreign Application Priority Data

Feb. 20, 2009  (JP) ................ 2009-037651
Nov. 13, 2009  (JP) ................ 2009-260183

(51) Int. Cl.
*A61L 15/60*    (2006.01)
*B01J 20/24*    (2006.01)
*A61K 38/00*    (2006.01)
*C07K 1/18*    (2006.01)
*C07K 1/22*    (2006.01)
*B01J 20/32*    (2006.01)
*B01J 41/20*    (2006.01)
*B01J 39/26*    (2006.01)
*C07K 1/16*    (2006.01)
*B01J 20/286*    (2006.01)
*B01D 15/38*    (2006.01)
*B01D 15/36*    (2006.01)

(52) U.S. Cl.
CPC ............ *C07K 1/16* (2013.01); *B01J 20/328* (2013.01); *B01J 41/20* (2013.01); *B01J 39/26* (2013.01); *B01D 15/3804* (2013.01); *B01D 15/362* (2013.01); *B01J 20/286* (2013.01)
USPC ............ 502/404; 530/412; 530/413; 530/416

(58) Field of Classification Search
None
See application file for complete search history.

(56) References Cited

U.S. PATENT DOCUMENTS

| 4,744,899 | A | 5/1988 | Tani et al. |
| 5,108,596 | A | 4/1992 | Ookuma et al. |
| 5,196,527 | A | 3/1993 | Ookuma et al. |
| 6,156,492 | A | 12/2000 | Kobayashi et al. |
| 2008/0203029 | A1 | 8/2008 | Deorkar et al. |
| 2008/0237124 | A1 | 10/2008 | Axen et al. |
| 2014/0128253 | A1* | 5/2014 | Umeda et al. ............ 502/404 |

FOREIGN PATENT DOCUMENTS

| JP | 60-500539 | 4/1985 |
| JP | 1-258739 | 10/1989 |
| JP | 3-277967 | 12/1991 |
| JP | 08-082303 | 3/1996 |
| JP | 10005329 | 1/1998 |
| JP | 2008-528966 | 7/2008 |
| JP | 2008-232764 | 10/2008 |
| JP | 2009-506340 | 2/2009 |
| WO | 84/03053 | 8/1984 |
| WO | 91/07427 | 5/1991 |
| WO | 2007/027139 A1 | 3/2007 |

OTHER PUBLICATIONS

International Search Report mailed May 18, 2010 in PCT/JP2010/052407 filed Feb. 18, 2010.
J. Horvath et al., "High-performance protein separations with novel strong ion exchangers", Journal of Chromatography A, vol. 679, pp. 11-22, (1994).
M. C. Stone et al., "Protein adsorption and transport in agarose and dextran-grafted agarose media for ion exchange chromatography", Journal of Chromatography A, vol. 1146, pp. 202-215, Apr. 6, 2007.

* cited by examiner

*Primary Examiner* — Daniel E Kolker
*Assistant Examiner* — James Rogers
(74) *Attorney, Agent, or Firm* — Drinker Biddle & Reath LLP

(57) ABSTRACT

The present invention provides a chromatography packing material having improved flow rate characteristics and adsorption characteristics. In particular, the present invention provides a chromatography packing material suitable for separation and purification of immunoglobulin in the manufacture of antibody preparations. A porous cellulose gel, which is made by adding polysaccharides having a limiting viscosity of 0.21 to 0.90 dL/g to porous cellulose particles, the dry weight per unit volume of the porous cellulose gel being 1.06 to 1.40 times the dry weight per unit volume of the porous cellulose particles, is used. By adding a predetermined amount of polysaccharides having a predetermined limiting viscosity to porous cellulose particles, flow rate characteristics and adsorption characteristics can be improved.

18 Claims, 1 Drawing Sheet

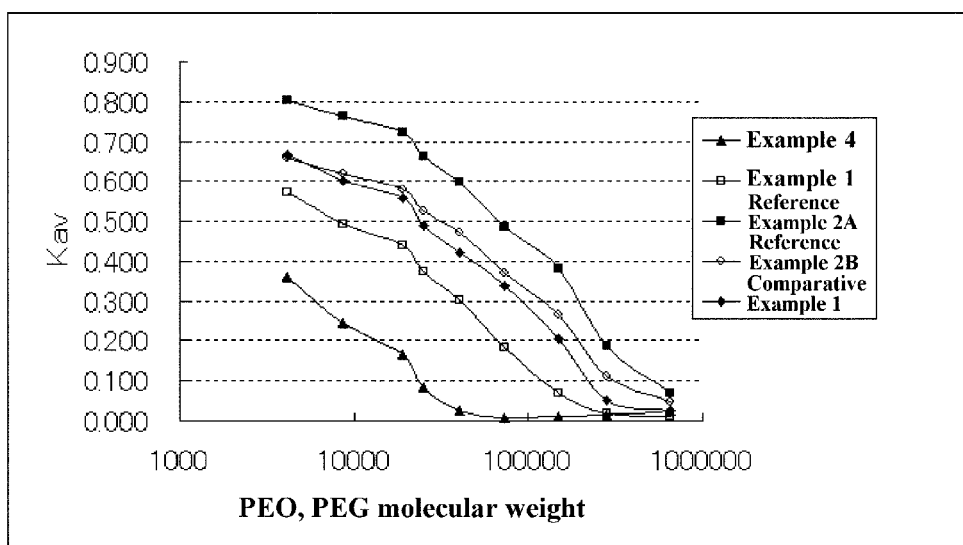

CELLULOSE GEL FOR PURIFICATION OF IMMUNOGLOBULIN

CROSS REFERENCE TO RELATED APPLICATIONS

This application is the National Stage of International Application No. PCT/JP2010/052407, filed Feb. 18, 2010, which claims benefit of Japanese Application No. 2009-037651, filed Feb. 20, 2009 and Japanese Application No. 2009-260183, filed Nov. 13, 2009, which are herein incorporated by reference in their entirety.

TECHNICAL FIELD

The present invention relates to a chromatography packing material, and particularly relates to production and use of a cation exchange chromatography packing material, which is suitable for separation and purification of immunoglobulin that can be utilized for antibody preparations and protein preparations such as biopharmaceuticals for blood preparations, etc.

BACKGROUND ART

Recently, productivity of protein preparations typified by antibody preparations has been improved through mass fermentation and high fermentation titer. With this, it is desired to improve efficiency of the purification process. In particular, improvement of flow rate characteristics and adsorption characteristics of chromatography packing materials to be used for purification is desired because cost reduction is led thereby.

In order to realize higher flow rates, chromatography packing materials produced using a technique of crosslinking a base gel to increase its strength have been developed. Moreover, it is known that adsorption characteristics are improved by combining these crosslinked gels with a hydrophilic polymer such as dextran. Such hydrophilic polymer-introduced porous base materials are attracting attention in the area of chromatography packing material development.

For example, Non-Patent Document 1 (Journal of Chromatography A, 679 (1994) 11-22) reports that adsorption performance for proteins is improved by using an ion exchange adsorbent made of dextran-derived hydrogel in which an ion exchange group is added to core particles made of polystyrene-silica (commercially available as "S HyperD (trademark)" (Biosepra, France)).

Further, Patent Document 1 (Japanese Laid-Open Patent Publication No. 2008-528966) reports that adsorption characteristics for proteins were improved by using a chromatography packing material made by adding polyethylenimine to methacrylate polymer particles.

Moreover, Patent Document 2 (Japanese Laid-Open Patent Publication No. 2008-232764) describes that a strong-cation ion exchange chromatography matrix having good flow rate characteristics was successfully obtained by introducing a ligand into a gel in which pullulan having a molecular weight of 500,000 was immobilized to porous methacrylate particles through 2-bromoethanesulfone. It is reported that in this case, the adsorption capacity of human immunoglobulin was 160 mg/ml.

Non-Patent Document 2 (Journal of Chromatography A, 1146 (2007) 202-215) reports the effects exerted when the surface of core particles made of agarose was modified using dextran. It is reported that by modifying the surface of core particles using dextran, diffusion characteristics of a target protein in a carrier is improved, resulting in improvement of mass transfer of the target. As an example of a chromatography packing material designed as described above, "SP Sepharose (trademark) XL" can be obtained from GE Healthcare Sciences.

Furthermore, Patent Document 3 (International Publication WO 2007/027139 pamphlet) reports that, as an example of a cation exchange chromatography gel matrix that can be utilized for production of antibody preparations, a gel having immunoglobulin (IgG) adsorption performance of 143 mg/ml was successfully obtained by introducing an ion exchange group into particles made by allowing dextran having a molecular weight of 40 kDa to be covalently bound a crosslinked agarose gel using vinyl sulfonic acid.

As described above, it has been reported that adsorption performance is improved by adding a hydrophilic polymer to a base gel. However, particularly in the field of the production of antibody preparations, improvement of high capacity and high titer in the production has been diligently practiced. Therefore, it is desired to further improve high flow rate characteristics and dynamic adsorption characteristics of base materials for purification.

Packing materials comprising silica as a base material, which are typical chromatography packing materials, are excellent in high flow rate characteristics. However, since the quality of materials thereof is unstable under alkali conditions, such packing materials are disadvantageous to general alkali washing.

On the other hand, chromatography packing materials using polysaccharides as base materials have high alkali resistance. Further, the chromatography packing materials using polysaccharides as base materials have porous property suitable for separation and purification of the protein size, and are promising materials for separation and purification of protein or vaccine preparations.

When making a comparison between cellulose and agarose, which are typical polysaccharides, cellulose has a robuster hydrogen-bonding network, and therefore advantageous for providing a higher flow rate desired for chromatography packing materials. However, in the case of using cellulose as a base material, flow rate characteristics and adsorption characteristics suitable for separation and purification of immunoglobulin for protein preparations and in particular, antibody preparations have not been realized.

PRIOR ART DOCUMENT

Patent Documents

Patent Document 1: Japanese Laid-Open Patent Publication No. 2008-528966
Patent Document 2: Japanese Laid-Open Patent Publication No. 2008-232764
Patent Document 3: International Publication WO 2007/027139 pamphlet Non-Patent Documents Non-Patent Document 1: Journal of Chromatography A, 679 (1994) 11-22
Non-Patent Document 2: Journal of Chromatography A, 1146 (2007) 202-215

SUMMARY OF THE INVENTION

Problems to be Solved by the Invention

Under the above-described circumstances, it is desired to provide a chromatography packing material having improved flow rate characteristics and adsorption characteristics. In particular, it is desired to provide a chromatography packing material suitable for separation and purification of immunoglobulin in the manufacture of antibody preparations, or a chromatography packing material in substitution for heparin gel.

Means for Solving the Problems

The present inventors diligently made researches and successfully obtained a chromatography packing material having desired flow rate characteristics and unprecedented adsorption characteristics with high values by introducing a cation exchange group into a base gel, which is made by adding a predetermined amount of polysaccharides to porous cellulose particles. In addition, in that process, the present inventors found that a chromatography packing material can be produced by an easier method when using polysaccharides having a high limiting viscosity.

That is, the present invention provides a porous cellulose gel, a chromatography packing material, and a production method and a use thereof, etc., as described below.

[1] A porous cellulose gel, which is made by adding polysaccharides having a limiting viscosity of 0.21 to 0.90 dL/g to porous cellulose particles, the dry weight per unit volume of the porous cellulose gel being 1.06 to 1.40 times the dry weight per unit volume of the porous cellulose particles.

[2] The porous cellulose gel according to item [1], wherein the porous cellulose particles have a particle diameter of 30 to 200 μm, and have a gel partition coefficient, which is represented by Kav when using standard polyethylene oxide having a weight average molecular weight of $1.5 \times 10^5$ Da and using pure water as a mobile phase, of 0.15 to 0.6.

[3] The porous cellulose gel according to item [1] or [2], wherein the polysaccharides are dextran.

[4] The porous cellulose gel according to item [1] or [2], wherein the polysaccharides are pullulan.

[5] The porous cellulose gel according to any one of items [1] to [4], wherein the porous cellulose particles are crosslinked cellulose particles having a water swelling degree of 5 to 20 ml/g.

[6] A chromatography packing material, which is made by adding a ligand to the porous cellulose gel according to any one of items [1] to [5].

[7] The packing material according to item [6], wherein the ligand is a sulfone group.

[8] The packing material according to item [7], wherein the introduction amount of the ligand is 0.13 to 0.30 mmol/ml in terms of the ion exchange capacity.

[9] The packing material according to item [6], wherein the ligand is a sulfate group.

[10] The packing material according to item [9], wherein the introduction amount of the ligand is 5000 to 60000 ppm in terms of the sulfur content.

[11] The packing material according to any one of items [6] to [8], which is used in purification of immunoglobulin.

[12] The packing material according to item [11], wherein the adsorption amount of immunoglobulin is 150 to 250 mg/ml.

[13] The packing material according to item [12], wherein the adsorption amount of immunoglobulin is 190 to 250 mg/ml.

[13a] The packing material according to item [9] or [10], which is for production of blood preparations.

[13b] The packing material according to item [9] or [10], which is for purification of immunoglobulin.

[14] A method for producing a chromatography packing material, comprising the step of adding a ligand to a porous cellulose gel, which is made by adding polysaccharides having a limiting viscosity of 0.21 to 0.90 dL/g to porous cellulose particles, the dry weight per unit volume of the porous cellulose gel being 1.06 to 1.40 times the dry weight per unit volume of the porous cellulose particles.

[15] The method according to item [14], wherein the porous cellulose particles have a particle diameter of 30 to 200 μm, and have a gel partition coefficient, which is represented by Kav when using standard polyethylene oxide having a weight average molecular weight of $1.5 \times 10^5$ Da and using pure water as a mobile phase, of 0.15 to 0.6.

[16] The method according to item [14] or [15], wherein the polysaccharides are dextran.

[17] The method according to item [14] or [15], wherein the polysaccharides are pullulan.

[18] A method for producing an immunoglobulin preparation, comprising the step of separating and purifying immunoglobulin using the packing material according to any one of items [6] to [8] and [11] to [13].

[18a] A method for producing a blood preparation, comprising the step of separating and purifying the blood preparation using the packing material according to item [9] or [10].

[18b] A method for producing an immunoglobulin preparation, comprising the step of separating and purifying immunoglobulin using the packing material according to item [9] or [10].

As used herein, "porous cellulose gel" is a separation agent for chromatography in a swelling state, in which porous particles, made by adding polysaccharides to porous cellulose particles, contain a solvent therein or absorb the solvent.

Advantageous Effect of the Invention

According to a preferred embodiment of the present invention, it is possible to provide a chromatography packing material having improved flow rate characteristics and adsorption characteristics and a base material that is suitably used therein.

According to a preferred embodiment of the present invention, by using dextran having a predetermined limiting viscosity as polysaccharides to be added to porous cellulose particles, a ligand can be efficiently introduced, and adsorption performance with respect to a target substance can be improved by a convenient method.

Further, according to a preferred embodiment of the present invention, by introducing a sufficient amount of a sulfone group as a ligand into the porous cellulose gel of the present invention, it is possible to provide a cation exchange chromatography gel which can be utilized for separation and purification of immunoglobulin in the field of antibody preparations. According to a preferred embodiment of the present invention, adsorption performance with respect to immunoglobulin can be significantly improved.

BRIEF DESCRIPTION OF THE DRAWINGS

FIG. 1 shows a graph in which the gel partition coefficients (Kav) of some of the exemplary wet gels obtained in the Examples and the Comparative Examples are plotted.

MODES FOR CARRYING OUT THE INVENTION

Hereinafter, the porous cellulose gel, the chromatography packing material, and the production method and the use thereof, etc., of the present invention will be descried in detail.

1. Porous Cellulose Gel

Firstly, the porous cellulose gel of the present invention will be described.

The porous cellulose gel of the present invention is made by adding polysaccharides having a limiting viscosity of 0.21 to 0.90 dL/g to porous cellulose particles, the dry weight per unit volume of the porous cellulose gel being 1.06 to 1.40 times the dry weight per unit volume of the porous cellulose particles.

The porous cellulose gel of the present invention is made by adding a predetermined amount of polysaccharides having a predetermined limiting viscosity to porous cellulose particles. When the surface or the inside of pores of the porous cellulose particles in which cellulose molecules are crosslinked by a crosslinking agent such as epichlorohydrin is modified by polysaccharides having a predetermined limiting viscosity, high flow rate characteristics are ensured in use for a chromatography packing material, and a ligand can be efficiently introduced, and therefore, high adsorption characteristics can be provided. Further, in the present invention, by using polysaccharides having a predetermined limiting viscosity, a desired amount of polysaccharides can be added to porous cellulose using an easy method.

The porous cellulose particles to be used in the present invention preferably have a particle diameter of 30 to 200 μm, and particularly preferably have a particle diameter of 50 to 150 μm. A desired particle diameter can be adjusted, for example, by sorting operation using a JIS standard sieve or the like. In particular, a sieve having a mesh size of 54 μm (wire diameter: 0.04 mm) and a sieve having a mesh size of 125 μm (wire diameter: 0.088 mm) are suitable for obtaining the particle diameter of the present invention.

The average particle diameter of the porous cellulose particles to be used in the present invention is preferably 80 to 120 μm, and more preferably 90 to 110 μm. The average particle diameter of the porous cellulose particles can be obtained by actually measuring photographs of a given number of cellulose particles taken using a scanning electron microscope or an optical microscope and calculating its average value. Specific measurement methods are as described in the Examples.

The sphericity (shorter diameter/longer diameter) of the porous cellulose particles to be used in the present invention is not particularly limited, but the porous cellulose particles preferably have a spherical shape of 0.8 to 1.0.

In order to add a predetermined amount of polysaccharides to the porous cellulose particles and to finally adsorb and collect a desired protein, the porous cellulose particles preferably have an appropriate pore size. As an index of porous property, the porous cellulose particles to be used in the present invention preferably have a gel partition coefficient, which is represented by Kav when using a commercially-available standard polyethylene oxide having a weight average molecular weight of $1.5 \times 10^5$ Da and using pure water as a mobile phase, of 0.15 to 0.6. The gel partition coefficient is more preferably 0.20 to 0.55, and even more preferably 0.25 to 0.50. Preferred examples of the standard polyethylene oxide having a weight average molecular weight of $1.5 \times 10^5$ Da include standard polyethylene oxide "SE-5" manufactured by Tosoh Corporation.

In the present invention, the gel partition coefficient "Kav" can be obtained using the following formula based on the relationship between the elution volume of the standard substance for molecular weight and the column volume:

$$Kav = (Ve - V_0)/(Vt - V_0)$$

[In the formula: Ve is a retention volume of a sample (ml); Vt is an empty column volume (ml); and $V_0$ is a retention volume of dextran T2000 (ml).]

The method for measuring the gel partition coefficient "Kav" is described, for example, in L. Fischer, Biochemical Experiment 2 (Seibutsu-Kagaku Jikken-Hou 2), "Gel Chromatography", 1st edition, Tokyo Kagaku Dozin Co., Ltd., etc. A specific measurement method is as described in the Examples.

The gel partition coefficient "Kav" of the porous cellulose particles of the present invention can be adjusted, for example, by controlling the dissolved cellulose concentration at the time of the production of cellulose particles as described in Reference Example 1 below. When using a crystalline cellulose "CEOLUS PH101" (trade name; Asahi Kasei Chemicals Corporation), by adjusting the concentration thereof to preferably 4 to 6% (W/W), the gel partition coefficient "Kav" suitable for the porous cellulose particles of the present invention can be obtained. Further, the gel partition coefficient "Kav" of the porous cellulose particles can also be controlled, for example, by controlling a method for crosslinking cellulose particles and crosslinking conditions. Preferably, by using the crosslinking method and conditions described in Reference Example 1 below for control, the gel partition coefficient "Kav" suitable for the porous cellulose particles of the present invention can be obtained. Naturally, it is possible to utilize a method in which the control of the dissolved cellulose concentration at the time of the production of cellulose particles is combined with the control of the method for crosslinking cellulose particles and the crosslinking conditions.

The porous cellulose particles to be used in the present invention may be crosslinked cellulose particles or non-crosslinked cellulose particles, but since higher flow rate characteristics can be obtained when a chromatography packing material is produced using the porous cellulose gel of the present invention as a base material, it is preferred to use crosslinked cellulose particles.

Crosslinked cellulose particles can be obtained by crosslinking non-crosslinked cellulose particles. Crosslinking is performed between free hydroxyl groups of cellulose molecules forming a three-dimensional net-like structure in each cellulose particle and functional groups of a crosslinking agent.

The method for producing crosslinked cellulose particles is not particularly limited. However, crosslinked cellulose particles can be produced by reacting a crosslinking agent with a suspension made by dispersing non-crosslinked cellulose particles in a solvent.

The solvent is not particularly limited as long as non-crosslinked cellulose particles can be dispersed therein, and it is possible to use any of water, an organic solvent such as alcohol, ketone, ether and aromatic hydrocarbon, and a mixture of water and the organic solvent. Among these solvents, a water-soluble solvent is preferred, and water is particularly preferred. Further, in order to improve the efficiency of crosslinking reaction, an inexpensive inorganic salt such as sodium sulfate may coexist with the suspension.

The crosslinking agent is not particularly limited as long as it is multifunctional, and in the present invention, a bifunctional crosslinking agent is preferably used. As the crosslinking agent to be used in the present invention, epichlorohydrin, polyethylene glycol or an epoxy compound made by glycidyl-etherifying hydroxyl groups of sorbitol, etc., are preferably exemplified, since bond with cellulose is chemically stable and charged groups which may cause undesired adsorption action at the time of reaction are not introduced. These crosslinking agents can be used solely or in combination. Among them, in the present invention, epichlorohydrin, which forms a stronger bond, is preferably used.

When using water as a solvent, crosslinking reaction is preferably performed in the presence of an alkali, and examples of the alkali include a hydroxide of an alkali metal such as sodium hydroxide and potassium hydroxide, and a hydroxide of an alkaline-earth metal such as calcium hydroxide. Among them, because of good solubility of a hydroxide of an alkali metal, sodium hydroxide and potassium hydroxide are preferred, and sodium hydroxide is particularly preferred.

As the method for producing crosslinked cellulose particles, more specifically, it is possible to use methods described, for example, in Japanese Publication for Opposition No. S43-10059, Japanese National-phase PCT Laid-Open Patent Publication No. 2000-508361, Japanese Laid-Open Patent Publication No. S60-39558, etc. In particular, it is preferred to use the method described in Reference Example 1 herein, since it is possible to obtain crosslinked cellulose particles having excellent flow rate characteristics with the porous property suitable for the present invention being retained. That is, crosslinked cellulose particles are preferably produced using a method comprising the step of continuously and dropwisely adding or portionwisely adding a crosslinking agent in an amount of 4 to 12 times the mole number of cellulose monomer and NaOH in an amount of 0.1 to 2 times the mole number of the crosslinking agent to a suspension made by dispersing non-crosslinked cellulose particles in water over 3 hours or more.

The water swelling degree of the porous cellulose particles to be used in the present invention is preferably 5 to 20 ml/g, and particularly preferably 6 to 13 ml/g.

In the present invention, the water swelling degree of the porous cellulose particles is defined as Volume/Weight of solid content (ml/g), and can be obtained in the following way: a gel swollen in water is put into a measuring cylinder and left while sometimes vibrated until its volume becomes constant, and after that, the volume is measured; subsequently, the gel is taken out from the measuring cylinder, and the total amount of the gel is dried; the dry weight of the porous cellulose particles is measured; and using the measured values, calculation is made based on the following formula:

Water swelling degree(ml/g)=Volume of gel(ml)÷Dry weight of gel(g)

The water swelling degree of the porous cellulose particles of the present invention can be adjusted, for example, by controlling the dissolved cellulose concentration at the time of the production of cellulose particles as described in Reference Example 1 below. When using a crystalline cellulose "CEOLUS PH101" (trade name; Asahi Kasei Chemicals Corporation), by adjusting the concentration thereof to preferably 4 to 6% (w/w), the water swelling degree suitable for the porous cellulose particles of the present invention can be obtained. Further, the water swelling degree of the porous cellulose particles can also be controlled by controlling a method for crosslinking cellulose particles and crosslinking conditions. Preferably, by using the crosslinking method and conditions described in Reference Example 1 below for control, the water swelling degree suitable for the porous cellulose particles of the present invention can be obtained. Naturally, it is possible to utilize a method in which the control of the dissolved cellulose concentration at the time of the production of cellulose particles is combined with the control of the method for crosslinking cellulose particles and the crosslinking conditions.

As the polysaccharides to be added to the porous cellulose particles in the present invention, those having a limiting viscosity of 0.21 to 0.90 dL/g are used. When the polysaccharides to be used in the present invention have the above-described limiting viscosity, a desired amount of the polysaccharides can be added to the porous cellulose particles. This allows a ligand to be efficiently introduced at the time of producing a chromatography packing material, and accordingly, adsorption characteristics with respect to a target substance can be improved. Moreover, when using the polysaccharides having the above-described limiting viscosity, there is an advantage that there is no load on the reaction operation. The range of the limiting viscosity of the polysaccharides to be used in a preferred embodiment of the present invention is, for example, 0.21 to 0.90 dL/g, and may be 0.21 to 0.80 dL/g or 0.21 to 0.70 dL/g, or may be 0.21 to 0.64 dL/g.

The limiting viscosity of the polysaccharides may be adjusted, for example, by selecting polysaccharides having an appropriate limiting viscosity from commercially-available polysaccharides. Alternatively, the limiting viscosity may be adjusted according to publicly-known methods (for example, a microorganism which produces polysaccharides having an appropriate limiting viscosity is selected and the polysaccharides are obtained from the microorganism, or culture conditions for a microorganism which produces polysaccharides are changed and the polysaccharides produced under the changed culture conditions are obtained).

In the present invention, the limiting viscosity of the polysaccharides can be obtained by obtaining viscosities of several polymer solutions each having a different concentration to measure the concentration dependence of the viscosities and extrapolating the obtained straight line to zero concentration according to Method 1 "Viscosity measurement by capillary tube viscometer" in Viscometric Methods in General Measurement Methods described in the 14th edition of the Japanese Pharmacopoeia.

It is known that the limiting viscosity of dextran satisfies the below-described relation equation with the weight average molecular weight, and therefore, the limiting viscosity of dextran can be obtained utilizing the weight average molecular weight:

Limiting viscosity($\eta$)=9×10$^{-4}$×Weight average molecular weight(Mw)$^{0.5}$ When the weight average molecular weight is used as a measure, the weight average molecular weight of the polysaccharides to be used in the present invention is more preferably 60 kDa or more, and even more preferably 70 kDa or more. Further, the weight average molecular weight of the polysaccharides is more preferably 500 kDa or less, and even more preferably 300 kDa or less.

Specific examples of the polysaccharides to be used in the present invention are not particularly limited as long as such polysaccharides do not have a charged group so as not to cause undesired nonspecific adsorption action at the time of reaction, can bind to the porous cellulose particles, and have a reactive functional group (preferably hydroxyl group), which allows introduction of a ligand after that. Examples of such polysaccharides include agarose, dextran, pullulan, starch and derivatives thereof. Among them, dextran is preferably used since it is advantageous in terms of its water solubility and reaction operability and can be obtained inexpensively. In another preferred embodiment of the present invention, pullulan is used as the polysaccharides.

In the present invention, the amount of the polysaccharides to be added to the porous cellulose particles is represented by a change amount of the dry weight per unit volume before and after addition of the polysaccharides. That is, in the present invention, the dry weight per unit volume of the porous cellulose gel is preferably 1.06 to 1.40 times the dry weight per unit volume of the porous cellulose particles. The preferred range of the ratio varies depending on the viscosity of the polysaccharides, but generally, the ratio is more preferably 1.10 times or more, even more preferably 1.15 times of more, and particularly preferably 1.20 times or more. When the adding amount of the polysaccharides is within the above-described ranges, a ligand can be efficiently introduced at the time of producing a chromatography packing material using the porous cellulose gel of the present invention, and adsorption characteristics with respect to a target substance can be improved.

The dry weight per unit volume of the porous cellulose gel and the dry weight per unit volume of the porous cellulose particles can be obtained in the following way.

Firstly, 10.0 g of the porous cellulose gel is added to a 50 ml measuring cylinder with a stopper, and pure water is added thereto to the 50 ml line. It is stoppered and allowed to stand until the volume becomes constant. After the volume becomes constant, the volume of the gel is read from the scale of the measuring cylinder.

Next, the gel is taken out from the measuring cylinder, the total amount of the gel is dried, and after that, the weight of the dried gel is measured.

Using the respective measured values, the dry weight per unit volume of the porous cellulose gel can be obtained according to the following formula:

Dry weight per unit volume(g/ml)=Dry weight of gel (g)÷Volume of gel(ml)

The dry weight per unit volume of the porous cellulose particles can be obtained in a manner similar to that described above. The specific measurement method is as described in the Examples.

The dry weight per unit volume of the porous cellulose gel and the dry weight per unit volume of the porous cellulose particles can be adjusted, for example, by selecting the molecular weight of the polysaccharides to be used, or by controlling the amount to be added to the porous cellulose particles.

In the present invention, the method for adding the polysaccharides to the porous cellulose particles is not particularly limited as long as it allows the polysaccharides to be bound to the porous cellulose particles via a chemical covalent bond. For example, the porous cellulose particles are reacted with a crosslinking agent in the presence of an alkali in a solvent, and then the obtained reaction product is reacted with the polysaccharides, thereby adding the polysaccharides to the porous cellulose particles. The crosslinking agent to be used for the reaction is not particularly limited as long as it is bifunctional or multifunctional, and the same as those used for crosslinking of the porous cellulose particles can be exemplified. In particular, epichlorohydrin is preferably used. As the alkali to be used for the reaction, the same as those used for crosslinking of the porous cellulose particles can be exemplified. The solvent to be used for the reaction is not particularly limited as long as it can disperse the porous cellulose particles. For example, the same as those used for crosslinking of the porous cellulose particles can be exemplified. Among them, water is particularly preferred. Further, in order to improve the reaction efficiency, an inorganic salt such as sodium sulfate may coexist with the reaction mixture.

As the method for adding the polysaccharides to the porous cellulose particles, the method described in Japanese Laid-Open Patent Publication No. S60-77769 may be used. That is, crosslinked cellulose particles are reacted with epichlorohydrin to introduce an epoxy group, and then reacted with dextran sulfate or a salt thereof, thereby adding dextran to the crosslinked cellulose particles. This method has an advantage in that unreacted dextran sulfate or a salt thereof can be collected and reused.

As described above, the polysaccharides having a predetermined limiting viscosity are added to the porous cellulose particles, thereby obtaining the porous cellulose gel of the present invention. By adding a ligand to the thus obtained porous cellulose gel of the present invention, desired flow rate characteristics can be provided, and in addition, it is possible to obtain a chromatography packing material having excellent adsorption characteristics with respect to a target substance.

2. Chromatography Packing Material

Next, the chromatography packing material of the present invention will be described.

The chromatography packing material of the present invention is made by adding a ligand to at least a part of reactive functional groups present in the aforementioned porous cellulose gel of the present invention. The porous cellulose gel of the present invention, which is made by adding a predetermined amount of the polysaccharides having a predetermined limiting viscosity to the porous cellulose particles, has excellent flow rate characteristics and allows a ligand to be efficiently introduced. Therefore, the chromatography packing material of the present invention made by adding the ligand to the porous cellulose gel has excellent flow rate characteristics and adsorption characteristics.

Affinity to a target compound is provided depending on the type and introduction amount of the ligand. Therefore, the type and introduction amount of the ligand may be suitably selected according to the intended use, etc. Examples of the ligand include an ion exchange group, a hydrophobic group, an affinity group, etc., and specific examples thereof include diethylamino, aminoethyl, carboxymethyl, sulfonethyl, sulfone, phenyl, a phosphate group, a sulfate group, a phenylborate group, Protein A and other reactive functional groups having an affinity.

The chromatography packing material of the present invention can be easily obtained by adding the ligand to at least a part of reactive functional groups in the porous cellulose gel of the present invention.

For example, by introducing a sulfone group into at least a part of reactive functional groups (e.g., hydroxyl groups) possessed by the porous cellulose gel of the present invention, a chromatography packing material suitable for separation and purification of protein such as lysozyme and immunoglobulin can be obtained. Alternatively, by introducing a sulfate group into at least a part of reactive functional groups (e.g., hydroxyl groups) possessed by the porous cellulose gel of the present invention, a chromatography packing material suitable for separation and purification of lysozyme, a blood coagulation factor IX, immunoglobulin, etc. can be obtained.

For example, introduction of a sulfone group into the porous cellulose gel of the present invention can be carried out in the below-described way.

Firstly, a sulfonation agent is put into a reaction container. Examples of the sulfonation agent include: haloalkanesulfonic acid such as sodium 3-chloro-2-hydroxypropanesulfonate and sodium 3-bromopropanesulfonate; 1,4-butanesultone; and sulfonic acid having epoxide such as 1,2-epoxyethanesulfonic acid. Among them, 1,4-butanesultone and sulfonic acid having epoxide such as 1,2-epoxyethanesulfonic acid is preferably used. The amount of the sulfonation agent to be used may be optionally selected depending on a target introduction rate of a sulfone group and the reaction conditions. For example, it is appropriate that the sulfonation agent is used in an amount of 0.001 to 1 equivalent per a reactive functional group in the porous cellulose gel.

Next, the dried porous cellulose gel is added to the sulfonation agent to cause reaction. The reaction temperature and the reaction time vary depending on the type of the solvent and the sulfonation agent, but the reaction is performed in an inert gas generally at 0 to 100° C., and preferably at 20 to 85° C., and preferably for 0.5 to 24 hours, and more preferably for 0.5 to 10 hours.

After the reaction is completed, the reaction mixture may be neutralized by adding an alkaline aqueous solution such as aqueous solution of sodium hydroxide thereto.

After that, the obtained reaction mixture is filtered or centrifuged to collect a product, and the product is washed with water until it becomes neutral, thereby obtaining a target substance. The introduction amount of the sulfone group can be adjusted by change of the amount of the sulfonation agent to be used, etc., and may be suitably determined depending on the intended use of the chromatography packing material, etc. Specifically, the introduction amount of the sulfone group can be increased by increasing the amount of the sulfonation agent to be used.

The method for introducing the sulfone group is described in detail in Japanese Laid-Open Patent Publication No. 2001-302702, Japanese Laid-Open Patent Publication No. H09-235301, etc.

The introduction amount of the ligand in the chromatography packing material of the present invention is not particularly limited, but since desired adsorption characteristics are provided, the introduction amount is preferably 0.13 to 0.30 mmol/ml, and particularly preferably 0.15 mmol/ml or more in terms of the ion exchange capacity. Further, it is particularly preferably 0.20 mmol/ml or less. As used herein, the "ion exchange capacity" means the molar quantity of ligand per volume of gel. The specific measurement method is as described in the Examples.

Further, introduction of a sulfate group into the porous cellulose gel of the present invention can be carried out in the below-described way.

For introduction of a sulfate group into the porous cellulose gel of the present invention, for example, it is possible to utilize the generally-known method disclosed in U.S. Pat. No. 4,480,091, Japanese Laid-Open Patent Publication No. 2006-274245, etc., i.e., a method for reacting chlorosulfonic acid with a sulfation agent in a solvent such as dimethylformamide and pyridine. The amount of the sulfation agent to be used at this time varies depending on the sulfur content of a target particle, but it is appropriate that the weight ratio between the cellulose gel and the sulfation agent (cellulose gel: sulfation agent) is in the range of 100:10 to 100:100, and preferably in the range of 100:10 to 100:50. The reaction varies depending on the type of the solvent and the sulfation agent, but is performed in an inert gas at 0 to 100° C., and preferably at 20 to 85° C. for 0.5 to 24 hours, and preferably for 0.5 to 10 hours.

After that, the obtained reaction mixture is filtered or centrifuged to collect a product, and the product is washed with water until it becomes neutral, thereby obtaining a target substance. The introduction amount of the sulfate group can be adjusted by the feed amount of the sulfation agent as described above, etc., and may be suitably determined depending on the intended use of the chromatography packing material, etc. Specifically, the introduction amount of the sulfate group can be increased by increasing the weight ratio of the sulfation agent to the cellulose gel.

The introduction amount of the sulfate group in the chromatography packing material of the present invention is not particularly limited, but since desired adsorption characteristics are provided, the introduction amount is preferably 5000 to 60000 ppm, and particularly preferably 10000 ppm or more in terms of the sulfur content. Further, it is particularly preferably 50000 ppm or less. As used herein, the "sulfur content" means the ratio of the weight of sulfur in the total dry weight of the porous cellulose gel. The specific measurement method is as described in the Examples.

The chromatography packing material of the present invention is particularly suitably used for separation and purification of immunoglobulin. By using the porous cellulose gel of the present invention, a desired amount of the sulfone group can be efficiently introduced, and therefore, affinity to immunoglobulin can be provided. According to a preferred embodiment of the present invention, the adsorption amount of immunoglobulin in the chromatography packing material of the present invention is 110 to 250 mg/ml. Moreover, according to a preferred embodiment of the present invention, by suitably adjusting the introduction amount of the sulfone group, it is possible to obtain the adsorption amount of immunoglobulin of 150 to 250 mg/ml, and more preferably 190 to 250 mg/ml, and as a result, it is possible to provide a chromatography packing material useful for separation and purification of immunoglobulin. As used herein, the "adsorption amount of immunoglobulin" means the adsorption amount of immunoglobulin per volume of gel measured according to the measurement method described in the Examples.

hromatography packing materials according to several embodiments of the present invention, in which the ligand is a sulfate group, can be suitably utilized as a chromatography packing material in substitution for heparin gel. The chromatography packing materials of these embodiments can be suitably used for separation and purification of various proteins such as lysozyme. The adsorption amount of lysozyme in the chromatography packing materials of these embodiments is preferably 50 to 250 mg/ml. Moreover, by suitably adjusting the introduction amount of the sulfate group, it is possible to obtain the adsorption amount of lysozyme of 100 to 250 mg/ml, and as a result, it is possible to provide a chromatography packing material useful for separation and purification of lysozyme. As used herein, the "adsorption amount of lysozyme" means the adsorption amount of lysozyme per volume of gel measured according to the measurement method described in the Examples.

Moreover, by separating and purifying immunoglobulin using the chromatography packing material of the present invention, a high-purity immunoglobulin preparation can be provided according to a simple method.

Alternatively, chromatography packing materials of some embodiments of the present invention are used as a chromatography packing material in substitution for heparin gel to separate and purify a blood preparation from plasma or the like, thereby providing the blood preparation according to a simple method.

Note that all the documents and publications cited herein are incorporated herein by reference in their entireties regardless of purposes thereof. In addition, the contents disclosed in the claims, specification and drawings of Japanese Patent Application No. 2009-37651 (filed on Feb. 20, 2009) and Japanese Patent Application No. 2009-260183 (filed on Nov. 13, 2009), to which priority is claimed by the present application, are incorporated herein.

EXAMPLES

Hereinafter, the present invention will be described in more detail based on working examples, but the present invention is not limited thereto.

Reference Example 1

Preparation of Crosslinked Cellulose Particles

Cellulose particles were produced as described below according to the method described in: Journal of Chromatography, 195 (1980), 221-230; and Japanese Laid-Open Patent Publication No. S55-44312, wherein the concentration of cellulose dissolved in a 60 wt % aqueous solution of calcium thiocyanate was set to 6% (w/w) or 10% (w/w).
(A) Production of 6% Spherical Cellulose Particles
(1) 6.4 g of crystalline cellulose (Asahi Kasei Chemicals Corporation, trade name: CEOLUS PH101) was added to 100 g of 60 wt % aqueous solution of calcium thiocyanate, and heated to 110 to 120° C. to be dissolved.
(2) To this solution, 6 g of sorbitan monooleate as a surfactant was added, and the mixture was added dropwise to 480 ml of o-dichlorobenzene that had been heated to 130 to 140° C. in advance, and this was stirred and dispersed at 200 to 300 rpm.
(3) Next, the above-described dispersion liquid was cooled to 40° C. or lower and poured into 190 ml of methanol, thereby obtaining a suspension of particles.
(4) The suspension was subjected to filtration and separation, and the particles were washed with 190 ml of methanol and subjected to filtration and separation. This washing operation was performed several times.
(5) The particles were further washed with a large amount of water, and then spherical cellulose particles of interest were obtained.
(6) Next, the spherical cellulose particles were screened to provide a desired particle size range (50 to 150 μm, average particle size: 100 μm).
(B) Production of 10% Spherical Cellulose Particles
10% spherical cellulose particles were obtained in a manner similar to that in the case of the production of the above-described 6% spherical cellulose particles except that 10.0 g of crystalline cellulose was used instead of 6.4 g of crystalline cellulose.
Next, the obtained cellulose particles were sorted by sieving operation using gauze sieves having a mesh size of 54 μm (wire diameter: 0.04 mm) and 125 μm (wire diameter: 0.088 mm).
The average particle diameter of the cellulose particles after sorted was 100 μm. The water swelling degree of 6% cellulose particles was 16.4 ml/g, and that of 10% cellulose particles was 9.6 ml/g.
Next, the obtained cellulose particles were crosslinked according to the below-described method.
(A) Preparation of Crosslinked 6% Cellulose Particles
(1) 100 g of 6% spherical cellulose particles obtained as described above (water content ratio: 10.8) was added to a solution obtained by dissolving 60 g of $Na_2SO_4$ in 121 g of pure water, and the mixture was stirred. The temperature of the mixture was adjusted to 50° C. and stirring was continued for 2 hours.
(2) Next, to this mixture, 3.3 g of 45 wt % aqueous solution of NaOH and 0.5 g of $NaBH_4$ were added, and the mixture was stirred. The initial alkali concentration [NaOH] was 0.69% (w/w).
(3) The mixture was continuously stirred at 50° C., while an amount obtained by dividing 48 g of 45 wt % aqueous solution of NaOH into 25 equal parts and an amount obtained by dividing 50 g of epichlorohydrin into 25 equal parts were respectively added thereto every 15 minutes over about 6 hours.
(4) After the addition was completed, the mixture was reacted at 50° C. for 16 hours.
(5) The mixture was cooled to 40° C. or lower, and then 2.6 g of acetic acid was added thereto for neutralization.
(6) The reaction mixture was filtered to collect a gel, and it was filtered and washed with pure water, thereby obtaining crosslinked 6% cellulose particles of interest.

Regarding the obtained crosslinked 6% cellulose particles, the water swelling degree, the average particle diameter, and Kav, which was measured using standard polyethylene oxide (Tosoh Corporation) "SE-5" (weight average molecular weight: $4.3 \times 10^4$ Da) or "SE-15" (weight average molecular weight: $1.5 \times 10^5$ Da) and using pure water as a mobile phase, were as follows:
Water swelling degree: 11.4 ml/g
Average particle diameter: 100 μm
Gel partition coefficient Kav: 0.38 (SE-15); 0.60 (SE-5)
(B) Preparation of Crosslinked 10% Cellulose Particles
(1) 100 g of 10% spherical cellulose particles obtained as described above (water content ratio: 6.3) was added to a solution obtained by dissolving 104 g of $Na_2SO_4$ in 282 g of pure water, and the mixture was stirred. The temperature of the mixture was adjusted to 50° C. and stirring was continued for 2 hours.
(2) Next, to this mixture, 5.7 g of 45 wt % aqueous solution of NaOH and 0.9 g of $NaBH_4$ were added, and the mixture was stirred. The initial alkali concentration [NaOH] was 0.69% (w/w).
(3) The mixture was continuously stirred at 50° C., while an amount obtained by dividing 83 g of 45 wt % aqueous solution of NaOH into 25 equal parts and an amount obtained by dividing 85 g of epichlorohydrin into 25 equal parts were respectively added thereto every 15 minutes over about 6 hours.
(4) After the addition was completed, the mixture was reacted at 50° C. for 16 hours.
(5) The mixture was cooled to 40° C. or lower, and then 4.0 g of acetic acid was added thereto for neutralization.
(6) The reaction mixture was filtered to collect a gel, and it was filtered and washed with pure water, thereby obtaining crosslinked 10% cellulose particles of interest.

Regarding the obtained crosslinked 10% cellulose particles, the water swelling degree, the average particle diameter, and Kav, which was measured using standard polyethylene oxide (Tosoh Corporation) "SE-5" (weight average molecular weight: $4.3 \times 10^4$ Da) or "SE-15" (weight average molecular weight: $1.5 \times 10^5$ Da) and using pure water as a mobile phase, were as follows:
Water swelling degree: 7.1 ml/g
Average particle diameter: 100 μm
Gel partition coefficient Kav: 0.27 (SE-15); 0.47 (SE-5)
Next, in order to add polysaccharides to the crosslinked cellulose particles, an epoxy group was introduced into the crosslinked cellulose particles in the below-described way.

Reference Example 2A

Epoxidation of Crosslinked 6% Cellulose Particles 200 g of the sucked/filtered crosslinked 6% cellulose particles were put into a 1 L separable flask. 160 ml of pure water was added thereto, and the flask was covered with a lid and put in a warm bath of 30° C. When the temperature of the inside of the flask reached 30° C., an aqueous solution of sodium hydroxide (54 g of sodium hydroxide, 133 g of pure water) and 120 g of epichlorohydrin were added thereto, and the mixture was stirred at 30° C. for 2 hours.

2 hours later, the reaction mixture was sucked and filtered, and the obtained wet gel was washed with 3 times its volume of pure water 5 times.

After washing, the obtained gel was sucked and filtered to remove excess water, and the gel was preserved in the wet state.

Reference Example 2B

Epoxidation of Crosslinked 10% Cellulose Particles

Epoxidation reaction was performed in a manner similar to that in Reference Example 2A except that the crosslinked 10% cellulose particles were used instead of the crosslinked 6% cellulose particles.

Next, dextran was added to the epoxidized crosslinked cellulose particles obtained in Reference Example 2A or 2B to obtain a porous cellulose gel, and this was further subjected to sulfonation treatment, thereby obtaining a chromatography packing material.

Example 1

To a 500 ml separable flask, 43 g of pure water and 32.0 g of Dextran 70 (Meito Sangyo Co. Ltd., limiting viscosity: 0.23 dL/g, weight average molecular weight: about 70,000) were added, and the mixture was stirred at room temperature until dissolution was completed.

After dissolution was completed, 60 g of the wet gel obtained in Reference Example 2A was added thereto, and the mixture was stirred at 30° C. for 1 hour. Next, to the flask, 6.6 g of 45% (w/w) aqueous solution of sodium hydroxide was added, and the mixture was stirred at 30° C. for 18 hours. 18 hours later, the reaction mixture was sucked and filtered, and the obtained wet gel was washed with 3 times its volume of pure water 5 times. After washing, the wet gel was sucked and filtered to remove excess water, and the gel was preserved in the wet state. Kav, which was obtained using standard polyethylene oxide (Tosoh Corporation) "SE-5" (weight average molecular weight: $4.3 \times 10^4$) and using pure water as a mobile phase, was 0.30. The ratio thereof to Kav of the crosslinked 6% cellulose obtained in Reference Example 1 (A) was 50%. Further, the dry weight per unit volume of the obtained wet gel was 1.06 times the dry weight per unit volume of the crosslinked 6% cellulose particles.

Further, 5 g of the obtained wet gel was put into a 50 ml conical flask with a stopper. Into this, 5 g of sodium sulfate (Wako Pure Chemical Industries, Ltd.) and aqueous solution of sodium hydroxide (0.98 g of sodium hydroxide, 7.8 g of pure water) were put, and it was stirred using an incubator at 50° C. for 30 minutes. 30 minutes later, 1.41 g of 1,4-butanesultone (Wako Pure Chemical Industries, Ltd.) was added thereto, and the mixture was stirred at 50° C. for 6 hours. 6 hours later, the reaction solution was sucked and filtered, and the obtained gel was washed with 5 times its volume of pure water 5 times. After washing, the obtained gel was sucked and filtered to remove excess water, and the gel was preserved in the wet state. In this way, the wet gel in which the sulfone group had been introduced as the ligand was obtained. At this time, the ion exchange capacity was 0.17 mmol/ml, and the γ-globulin 10% dynamic adsorption capacity was 146 mg/ml.

Example 2

A wet gel was obtained in a manner similar to that in Example 1, except that Dextran 70 was used in an amount of 24.8 g. Kav, which was obtained using standard polyethylene oxide (Tosoh Corporation) "SE-5" (weight average molecular weight: $4.3 \times 10^4$) and using pure water as a mobile phase, was 0.37. The ratio thereof to Kav of the crosslinked 6% cellulose obtained in Reference Example 1 (A) was 62%. Further, the dry weight per unit volume of the obtained wet gel was 1.09 times the dry weight per unit volume of the crosslinked 6% cellulose particles.

Further, in a manner similar to that in Example 1, 1.28 g of 1,4-butanesultone was used to sulfonate the obtained gel, and the gel was preserved in the wet state. At this time, the ion exchange capacity was 0.13 mmol/ml, and the γ-globulin 10% dynamic adsorption capacity was 122 mg/ml.

Example 3

A wet gel was obtained in a manner similar to that in Example 1, except that 17.5 g of Polymer Dextran EH (Meito Sangyo Co. Ltd., limiting viscosity: 0.42 dL/g, weight average molecular weight: about 178,000 to 218,000) was used instead of Dextran 70. Kav, which was obtained using standard polyethylene oxide (Tosoh Corporation) "SE-5" (weight average molecular weight: $4.3 \times 10^4$) and using pure water as a mobile phase, was 0.17. The ratio thereof to Kav of the crosslinked 6% cellulose obtained in Reference Example 1 (A) was 28%. Further, the dry weight per unit volume of the obtained wet gel was 1.11 times the dry weight per unit volume of the crosslinked 6% cellulose particles.

Further, in a manner similar to that in Example 1, 1.39 g of 1,4-butanesultone was used to sulfonate the obtained gel, and the gel was preserved in the wet state. At this time, the ion exchange capacity was 0.15 mmol/ml, and the γ-globulin 10% dynamic adsorption capacity was 124 mg/ml.

Example 4

A wet gel was obtained in a manner similar to that in Example 1, except that 33.0 g of Polymer Dextran EH was used instead of Dextran 70. Kav, which was obtained using standard polyethylene oxide (Tosoh Corporation) "SE-5" (weight average molecular weight: $4.3 \times 10^4$) and using pure water as a mobile phase, was 0.03. The ratio thereof to Kav of the crosslinked 6% cellulose obtained in Reference Example 1 (A) was 5%. Further, the dry weight per unit volume of the obtained wet gel was 1.34 times the dry weight per unit volume of the crosslinked 6% cellulose particles.

Further, in a manner similar to that in Example 1, 1.57 g of 1,4-butanesultone was used to sulfonate the obtained gel, and the gel was preserved in the wet state. At this time, the ion exchange capacity was 0.19 mmol/ml, and the γ-globulin 10% dynamic adsorption capacity was 241 mg/ml.

Example 5

A wet gel was obtained in a manner similar to that in Example 1, except that 10.9 g of Dextran T500 (Pharmacosmos, weight average molecular weight: 500 kDa, limiting viscosity: 0.64 dL/g,) was used instead of Dextran 70. Kav, which was obtained using standard polyethylene oxide (Tosoh Corporation) "SE-5" (weight average molecular weight: $4.3 \times 10^4$) and using pure water as a mobile phase, was 0.21. The ratio thereof to Kav of the crosslinked 6% cellulose obtained in Reference Example 1 (A) was 35%. Further, the dry weight per unit volume of the obtained wet gel was 1.10 times the dry weight per unit volume of the crosslinked 6% cellulose particles.

Further, in a manner similar to that in Example 1, 1.29 g of 1,4-butanesultone was used to sulfonate the obtained gel, and the gel was preserved in the wet state. At this time, the ion exchange capacity was 0.14 mmol/ml, and the γ-globulin 10% dynamic adsorption capacity was 117 mg/ml.

Example 6

A wet gel was obtained in a manner similar to that in Example 1, except that 17.3 g of Dextran T500 was used instead of Dextran 70. Kav, which was obtained using standard polyethylene oxide (Tosoh Corporation) "SE-5" (weight average molecular weight: $4.3 \times 10^4$) and using pure water as a mobile phase, was 0.17. The ratio thereof to Kav of the crosslinked 6% cellulose obtained in Reference Example 1 (A) was 28%. Further, the dry weight per unit volume of the obtained wet gel was 1.22 times the dry weight per unit volume of the crosslinked 6% cellulose particles.

Further, in a manner similar to that in Example 1, 1.41 g of 1,4-butanesultone was used to sulfonate the obtained gel, and the gel was preserved in the wet state. At this time, the ion exchange capacity was 0.14 mmol/ml, and the γ-globulin 10% dynamic adsorption capacity was 199 mg/ml.

Example 7

A wet gel was obtained in a manner similar to that in Example 1, except that 24.5 g of Dextran T500 was used instead of Dextran 70. Kav, which was obtained using standard polyethylene oxide (Tosoh Corporation) "SE-5" (weight average molecular weight: $4.3 \times 10^4$) and using pure water as a mobile phase, was 0.02. The ratio thereof to Kav of the crosslinked 6% cellulose obtained in Reference Example 1 (A) was 3%. Further, the dry weight per unit volume of the obtained wet gel was 1.34 times the dry weight per unit volume of the crosslinked 6% cellulose particles.

Further, in a manner similar to that in Example 1, 1.55 g of 1,4-butanesultone was used to sulfonate the obtained gel, and the gel was preserved in the wet state. At this time, the ion exchange capacity was 0.17 mmol/ml, and the γ-globulin 10% dynamic adsorption capacity was 217 mg/ml.

Comparative Example 1

A wet gel was obtained in a manner similar to that in Example 1, except that 33 g of Dextran 40 (Meito Sangyo Co. Ltd., limiting viscosity: 0.17 dL/g, weight average molecular weight: about 40,000) was used instead of Dextran 70. Kav, which was obtained using standard polyethylene oxide (Tosoh Corporation) "SE-5" (weight average molecular weight: $4.3 \times 10^4$) and using pure water as a mobile phase, was 0.42. The ratio thereof to Kav of the crosslinked 6% cellulose obtained in Reference Example 1 (A) was 70%. Further, the dry weight per unit volume of the obtained wet gel was 1.10 times the dry weight per unit volume of the crosslinked 6% cellulose particles.

Further, in a manner similar to that in Example 1, 1.29 g of 1,4-butanesultone was used to sulfonate the obtained gel, and the gel was preserved in the wet state. At this time, the ion exchange capacity was 0.13 mmol/ml, and the γ-globulin 10% dynamic adsorption capacity was 101 mg/ml.

Comparative Example 2

A wet gel was obtained in a manner similar to that in Example 1, except that Dextran 70 (Meito Sangyo Co. Ltd., limiting viscosity: 0.23 dL/g, weight average molecular weight: about 70,000) was used in an amount of 17.5 g. Kav, which was obtained using standard polyethylene oxide (Tosoh Corporation) "SE-5" (weight average molecular weight: $4.3 \times 10^4$) and using pure water as a mobile phase, was 0.43. The ratio thereof to Kav of the crosslinked 6% cellulose obtained in Reference Example 1 (A) was 72%. Further, the dry weight per unit volume of the obtained wet gel was 1.04 times the dry weight per unit volume of the crosslinked 6% cellulose particles.

Further, in a manner similar to that in Example 1, 1.23 g of 1,4-butanesultone was used to sulfonate the obtained gel, and the gel was preserved in the wet state. At this time, the ion exchange capacity was 0.13 mmol/ml, and the γ-globulin 10% dynamic adsorption capacity was 70 mg/ml.

Comparative Example 3

A wet gel was obtained in a manner similar to that in Example 1, except that 11.0 g of Polymer Dextran EH (Meito Sangyo Co. Ltd., limiting viscosity: 0.42 dL/g, weight average molecular weight: about 200,000) was used instead of Dextran 70. Kav, which was obtained using standard polyethylene oxide (Tosoh Corporation) "SE-5" (weight average molecular weight: $4.3 \times 10^4$) and using pure water as a mobile phase, was 0.32. The ratio thereof to Kav of the crosslinked 6% cellulose in Reference Example 1 was 53%. Further, the dry weight per unit volume of the obtained wet gel was 1.05 times the dry weight per unit volume of the crosslinked 6% cellulose particles.

Further, in a manner similar to that in Example 1, 1.26 g of 1,4-butanesultone was used to sulfonate the obtained gel, and the gel was preserved in the wet state. At this time, the ion exchange capacity was 0.12 mmol/ml, and the γ-globulin 10% dynamic adsorption capacity was 76 mg/ml.

The results of Examples 1-7 and Comparative Examples 1-3 are shown in Table 1.

TABLE 1

| | Viscosity (dL/g) | Kav obtained using standard polyethylene oxide SE-5 | Ratio to Kav of 6% crosslinked gel (%) | Ion exchange capacity (mmol/ml) | γ-globulin 10% dynamic adsorption capacity (mg/ml) | Ratio of dry weight after addition of dextran to dry weight before addition of dextran (%) |
|---|---|---|---|---|---|---|
| Example 1 | 0.23 | 0.30 | 50 | 0.17 | 146 | 106 |
| Example 2 | 0.23 | 0.37 | 62 | 0.13 | 122 | 109 |
| Example 3 | 0.42 | 0.12 | 20 | 0.15 | 124 | 111 |
| Example 4 | 0.42 | 0.03 | 5 | 0.19 | 241 | 134 |

TABLE 1-continued

|  | Viscosity (dL/g) | Kav obtained using standard polyethylene oxide SE-5 | Ratio to Kav of 6% crosslinked gel (%) | Ion exchange capacity (mmol/ml) | γ-globulin 10% dynamic adsorption capacity (mg/ml) | Ratio of dry weight after addition of dextran to dry weight before addition of dextran (%) |
|---|---|---|---|---|---|---|
| ExaMple 5 | 0.64 | 0.21 | 35 | 0.14 | 117 | 110 |
| Example 6 | 0.64 | 0.17 | 28 | 0.14 | 199 | 122 |
| Example 7 | 0.64 | 0.02 | 3 | 0.17 | 217 | 134 |
| Comparative Example 1 | 0.17 | 0.42 | 70 | 0.13 | 101 | 110 |
| Comparative Example 2 | 0.23 | 0.43 | 72 | 0.13 | 70 | 104 |
| Comparative Example 3 | 0.42 | 0.32 | 53 | 0.12 | 76 | 105 |

As shown in Table 1, the numerical values of the γ-globulin adsorption amounts of the porous cellulose gels obtained in the Examples are significantly higher than those of the Comparative Examples.

In the above-described Examples and Comparative Examples, the γ-globulin 10% dynamic adsorption capacity, Kav, the amount of change of the dry weight before and after addition of dextran, the ion exchange capacity and the average particle diameter were obtained according to the below-described measurement methods 1-5.

[Measurement Method 1]

Measurement of dynamic adsorption capacity using γ-globulin (1) Instrument and Reagent Used LC system: BioLogicLP (BIORAD)

Buffer: Acetic acid buffer PH 4.3, 0.05 M NaCl

Antibody: γ-globulin, derived from human serum (Wako Pure Chemical Industries, Ltd.)

Column: Glass column having an inner diameter of 5 mm and a length of 50 mm (EYELA)

(2) Measurement Method

Firstly, the antibody was dissolved in the buffer to prepare an antibody solution of 1 mg/ml. Further, the column was filled with the ion exchange group-added gel with no space. Next, the column was connected to the system, and using the buffer, equilibration was performed with a flow rate of 1 ml/min. until UV (ultraviolet absorbance: 280 nm) and the electrical conductivity of the column effluent became constant. After that, UV of the baseline was adjusted to zero. The antibody solution was flowed from the bypass line and the flow path to the column was substituted with the antibody solution. Next, switching from the bypass line to the line to the column was carried out, and the antibody solution was flowed into the column with a flow rate of 1 ml/min. UV of the column effluent was monitored, and when UV of the column effluent reached 10% of UV of the antibody solution measured in advance, flow of the antibody solution was stopped. The 10% dynamic adsorption capacity was obtained using the below-described formula. This analysis was carried out in a room at 20° C.

{Concentration of antibody solution(mg/ml)×Time from when flow of antibody solution is started till when flow is stopped(min)×Flow rate(ml/min)−Capacity of empty column}/Volume of column=10% dynamic adsorption capacity(mg/ml)

[Measurement Method 2]

Measurement of gel partition coefficient Kav of porous cellulose gel (1) Instrument and Reagent Used Column: Empty column ¼×4.0 mm I.D×300 mm, 10F (Tosoh Corporation)

Reservoir: Packe·⅜ (Tosoh Corporation)

Pump: POMP P-500 (Pharmacia)

Pressure meter: AP-53A (KEYENCE)

(2) Method for Filling Column

The column was connected to the reservoir, and an end fitting was connected to the lower portion of the column. For the measurement of Kav, 15 g of the gel that had been filtered under reduced pressure and in the wet state was prepared and put into a 50 ml beaker. To this, 20 ml of ultrapure water was added and briefly stirred. The mixture, which was in a state in which the particles or gel were dispersed in the solution, was slowly added to the column so that the mixture flowed on the wall of the reservoir. The gel remaining in the beaker was rinsed with a small amount of ultrapure water and slowly added to the column. After that, ultrapure water was added to nearly reach the upper portion of the reservoir, and the reservoir was covered with a lid. An adapter was connected to the upper portion of the reservoir, and ultrapure water was delivered using a pump. The pressure meter was connected to the middle of the delivery line in advance, and the pressure was monitored. The flow rate was increased until the pressure became 0.3 MPa, and after that, ultrapure water was flowed for 30 minutes to fill the reservoir. After the reservoir was filled, the pump was stopped and the adapter and the lid of the reservoir were removed. Next, ultrapure water in the reservoir was sucked out by a pipette. The reservoir was removed, the gel protruding from the column was removed, and the end fitting was connected.

The method for obtaining the gel partition coefficient Kav of the porous cellulose particles is the same as the method used for the porous cellulose gel.

(3) Kav Measurement Apparatuses

System: SCL-10APVP (SHIMAZU)

Workstation: CLASS-VP (SHIMAZU)

RI detector: RID-10A (SHIMAZU)

Pump: LC-10AT (SHIMAZU)

Autoinjector: SIL-10ADVP (SHIMAZU)

(4) Kav Measurement Samples

1. Dextran T2000 (Pharmacia)
2. SE-70 (Tosoh Corporation), molecular weight: $5.8 \times 10^5$
3. SE-30 (Tosoh Corporation), molecular weight: $3.0 \times 10^5$
4. SE-15 (Tosoh Corporation), molecular weight: $1.5 \times 10^5$
5. SE-8 (Tosoh Corporation), molecular weight: $1.01 \times 10^5$ 6. SE-5 (Tosoh Corporation), molecular weight: $4.3 \times 10^4$
7. SE-2 (Tosoh Corporation), molecular weight: $2.77 \times 10^4$
8. PEG19000 (SCIENTIFIC POLYMER PRODUCTS), molecular weight: 19700
9. PEG8650 (POLYMER LABORATORIES), molecular weight: 8650
10. PEG4120 (POLYMER LABORATORIES), molecular weight: 4120

(5) Formula for Obtaining Kav $$Kav=(Ve-V_0)/(Vt-V_0)$$

[In the formula, Ve represents a retention capacity of a sample (ml), Vt represents a volume of an empty column (ml), and $V_0$ represents a retention capacity of Dextran T2000 (ml).]

(6) Measurement Results

One example of the plot of Kav is shown in FIG. 1.

[Measurement Method 3]

Measurement of Change Amount of Dry Weight Before and after Addition of Dextran 10.0 g of the crosslinked cellulose particles obtained in Reference Example 1 are added to a 50 ml measuring cylinder with a stopper, and pure water is added thereto to the 50 ml line. It is stoppered and allowed to stand until the volume becomes constant. After the volume becomes constant, the volume of the gel is read from the scale of the measuring cylinder.

Next, the gel is taken out from the measuring cylinder, the total amount of the gel is dried in an oven at 80° C. for 16 hours, and after that, the weight of the dried gel is measured. Using the measured values, the dry weight per unit volume of the crosslinked cellulose particles can be obtained according to the following formula:

Dry weight per unit volume(g/ml)=Dry weight of gel (g)÷Volume of gel (ml)

Regarding the wet gel after the dextran addition reaction, the dry weight per unit volume (g/ml) is obtained in the same way, and a change of dry weight relative to the dry weight per unit volume of the crosslinked cellulose particles is calculated.

[Measurement Method 4]

Method for Measuring Ion Exchange Capacity 1 ml of the butanesultone-added wet gel was weighed and put into a beaker, and 0.5 mol/l of hydrochloric acid (Wako Pure Chemical Industries, Ltd.) was added thereto and stirred for 3 minutes. After that, the mixture was sucked and filtered to remove hydrochloric acid, and the mixture was washed with pure water.

1 ml of the washed gel was added to a beaker, and 3 ml of 0.1 mol/l aqueous solution of sodium hydroxide (Wako Pure Chemical Industries, Ltd.) and 1 drop of phenolphthalein solution were added thereto. To this solution, 0.1 mol/l hydrochloric acid (Wako Pure Chemical Industries, Ltd.) was added until the color of the solution became a transparent color. When the amount of hydrochloric acid added until the solution became a transparent color is regarded as X ml, the ion exchange capacity (IEC) per 1 ml of gel can be calculated using the following formula:

(0.1×3/1000−0.1×X/1000)×1000(mmol/ml)

[Measurement Method 5]

Measurement of Average Particle Diameter

Wet cellulose particles were put on a slide glass and photographed using an optical microscope (×100). Using the photograph, the diameter of each of 200 arbitrary particles was measured, and the average value thereof was regarded as an average particle diameter.

Example 8

Working Example of 10% Crosslinked Gel

A wet gel was obtained in a manner similar to that in Example 1, except that the crosslinked 10% cellulose particles obtained in Reference Example 2B were used instead of the crosslinked 6% cellulose particles and Dextran 70 was used in an amount of 54 g. At this time, the amount of dextran added was 16.3 mg/ml. Kav, which was obtained using standard polyethylene oxide (Tosoh Corporation) "SE-5" (weight average molecular weight: $4.3 \times 10^4$) and using pure water as a mobile phase, was 0.24. The ratio thereof to Kav of the crosslinked 10% cellulose obtained in Reference Example 1 (B) was 51%. Further, the dry weight per unit volume of the obtained wet gel was 1.10 times the dry weight per unit volume of the crosslinked 10% cellulose particles.

5 g of the obtained wet gel was put into a 50 ml conical flask with a stopper. Into this, 5 g of sodium sulfate (Wako Pure Chemical Industries, Ltd.) and aqueous solution of sodium hydroxide (1.55 g of sodium hydroxide, 15.37 g of pure water) were put, and it was stirred using an incubator at 50° C. for 30 minutes. 30 minutes later, 4.11 g of 1,4-butanesultone (Wako Pure Chemical Industries, Ltd.) was added thereto, and the mixture was stirred at 50° C. for 6 hours. 6 hours later, the reaction mixture was sucked and filtered, and the obtained gel was washed with 5 times its volume of pure water 5 times. After washing, the obtained gel was sucked and filtered to remove excess water, and the gel was preserved in the wet state. At this time, the ion exchange capacity was 0.28 mmol/ml, and the γ-globulin 10% dynamic adsorption capacity was 125 mg/ml.

According to the above-described results, it was demonstrated that it is possible to obtain a chromatography packing material that can efficiently separate and purify immunoglobulin when using the 10% crosslinked cellulose particles like the case of using the 6% crosslinked cellulose particles.

Example 9

To a 500 ml separable flask, 40 g of pure water and 24 g of pullulan (Hayashibara Co., Ltd., cosmetic pullulan, limiting viscosity: 0.73 dL/g) were added, and the mixture was stirred at room temperature until dissolution was completed.

After dissolution was completed, 60 g of the wet gel obtained in Reference Example 2A was added thereto, and the mixture was stirred at 30° C. for 1 hour. Next, to the flask, 6.4 g of 45% (w/w) aqueous solution of sodium hydroxide was added, and the mixture was stirred at 30° C. for 18 hours. 18 hours later, the reaction mixture was sucked and filtered, and the obtained wet gel was washed with 3 times its volume of pure water 5 times. After washing, the wet gel was sucked and filtered to remove excess water, and the gel was preserved in the wet state. The dry weight per unit volume of the obtained wet gel was 1.24 times the dry weight per unit volume of the crosslinked 6% cellulose particles.

Further, 8 g of the obtained wet gel was put into a 50 ml conical flask with a stopper. Into this, 8.9 g of sodium sulfate (Wako Pure Chemical Industries, Ltd.) and aqueous solution of sodium hydroxide (1.8 g of sodium hydroxide, 15 g of pure water) were put, and it was stirred in an incubator at 50° C. for 30 minutes. 30 minutes later, 1.2 g of 1,4-butanesultone (Wako Pure Chemical Industries, Ltd.) was added thereto, and the mixture was stirred at 50° C. for 6 hours. 6 hours later, the reaction solution was sucked and filtered, and the obtained gel was washed with 5 times its volume of pure water 5 times. After washing, the obtained gel was sucked and filtered to remove excess water, and the gel was preserved in the wet state. In this way, the wet gel in which the sulfone group had been introduced as the ligand was obtained. At this time, the ion exchange capacity was 0.13 mmol/ml, and the γ-globulin 10% dynamic adsorption capacity was 178 mg/ml.

As understood from the comparison with Example 6, the value of the 7-globulin adsorption amount was high even when pullulan was used as polysaccharides instead of dextran.

Example 10-1

Introduction of Sulfate Ligand

To 100 g of a wet gel, which was obtained by reacting with Polymer Dextran EH in a manner similar to that in Example 4, 300 g of methanol was added, and the mixture was stirred at room temperature for 10 minutes, and then it was sucked and filtered. This operation was repeated 5 times to obtain a methanol-substituted gel. The gel was vacuum-dried at 50 to 60° C. until the water content became 2.5 (w/w). In a 500 ml separable flask, 200 g of pyridine was stirred and cooled to 10° C. or lower, and after that, 4 g of chlorosulfonic acid was added dropwise thereto under nitrogen atmosphere. After the addition was completed, the mixture was reacted at 10° C. or lower for 1 hour, and then heated to 65° C. After the temperature reached 65° C., 30 g of the dried gel was added, and the mixture was reacted while stirred for 4 hours. After the reaction was completed, the mixture was left at 25° C. overnight. After that, 20% w/w NaOH was added thereto for neutralization. The reaction mixture was filtered to collect a gel, and the gel was washed with pure water until it became neutral, thereby obtaining a wet gel having the sulfate group as the ligand.

Example 10-2

The adsorption amount of lysozyme of the wet gel in Example 10-1, which was measured according to the below-described measurement method 6, was 97 mg per 1 ml of the gel. Further, the sulfation degree (sulfur content) of the gel obtained according to the below-described measurement method 7 was 22200 ppm.

The dextran-added porous cellulose gel of the working example can be utilized as a chromatography packing material in which the ligand is, for example, sulfate. In the gel of the working example, the ligand is sulfated dextran, and therefore, the gel can also be utilized as a chromatography packing material in substitution for heparin gel.

[Measurement Method 6]
Measurement of Adsorption Amount of Lysozyme

A column having an inner diameter of 7 mm was filled with 1 ml of the wet gel of the above-described Example 10-1, and using 0.05 M Tris-HCl buffer (pH 9.5), equilibration was performed with a flow rate of 50 ml/h for 0.6 hour. 0.05 M Tris-HCl buffer (pH 9.5) was added to lysozyme (Wako Pure Chemical Industries, Ltd.) to be dissolved so that the concentration became 5.0 mg/ml, and 100 ml of the solution was flowed through the gel in the column with a flow rate of 50 ml/h to allow the gel to adsorb lysozyme. Further, the gel was washed with 0.05 M Tris-HCl buffer (pH 9.5) with a flow rate of 50 ml/h. Total amounts of the lysozyme solution and the washing solution that had been passed through the gel were collected and diluted to 250 ml in total. The adsorption amount of lysozyme of the gel in the column was obtained from the difference between the lysozyme before adsorption and the lysozyme after adsorption calculated based on the absorbance at 280 nm. Specifically, each of the lysozyme solutions was diluted 10-fold, and the absorbance of each of the obtained solutions at 280 nm was as follows:

Absorbance $A280$ of 5.0 mg/ml lysozyme solution=1.250

Absorbance $A280$ of solution passed through the gel+ washing solution used for the gel=0.397

Adsorption amount of lysozyme(mg/ml-gel)=5.0× 100−5.0×(0.397/01.250)×250=103

[Measurement Method 7]
Measurement of Sulfation Degree (Sulfur Content)

The sulfur content was obtained using the below-described method according to the "ion chromatography method" (document name: Analytical Chemistry Handbook (Bunseki Kagaku Binran), 5th revised edition, p. 30 (Japan Society for Analytical Chemistry Ed.)). A sample was vacuum-dried at 60° C. for 16 to 20 hours and mashed using a mortar, and further dried at 105° C. for 2 hours. To 0.05 g of the dried sample, 2.5 ml of 2M hydrochloric acid was added, and the mixture was hydrolyzed at 110° C. for 16 hours. After it was iced, 1 ml of the supernatant solution was collected and neutralized using 2M aqueous solution of sodium hydroxide, and it was diluted to 25 ml in total. As a column, ICS-A-23 manufactured by Yokogawa Electric Corporation was used. The temperature of an oven was set at 40° C. As an eluant, 3 mM $Na_2CO_3$ solution was used with a flow rate of 1 ml/min., and as a scavenger, 15 mM sulfuric acid was used with a flow rate of 1 ml/min. IC7000 ion chromato analyzer manufactured by Yokogawa Electric Corporation was used for analysis, and the $SO_4$ concentration was calculated based on the standard curve plotted with the standard solutions described below. The blank value is a value obtained by the same operation without adding the dried sample. 2 μg/ml standard $SO_4$ solution (Kanto Chemical Company, mixed anion standard solution IV) was used as the standard solution of this measurement method, subjected to serial dilution, and analyzed by the ion chromato analyzer under the same conditions to plot a standard curve. The ion content was calculated using the following formula:

Sulfur content(ppm)=$(X_{sample}-X_{blank})$×25×2.5× 0.3333/0.05(sample amount: g)

In the above-described formula, $X_{sample}$ and $X_{blank}$ are concentrations (ppm) calculated from the standard curve obtained using the standard $SO_4$ solution.

INDUSTRIAL APPLICABILITY

The chromatography packing material of the present invention has excellent flow rate characteristics and adsorption characteristics with respect to a target substance, and therefore is useful as a packing material for separation and purification of a target substance in various fields. The chromatography packing material according to the preferred embodiment of the present invention has particularly excellent adsorption performance with respect to immunoglobulin, and therefore is suitably used for separation and purification of antibody preparations.

The invention claimed is:

1. A porous cellulose gel, which is made by adding polysaccharides having a limiting viscosity of 0.21 to 0.90 dL/g to porous cellulose particles, the dry weight per unit volume of the porous cellulose gel being 1.06 to 1.40 times the dry weight per unit volume of the porous cellulose particles.

2. The porous cellulose gel according to claim 1, wherein the porous cellulose particles have a particle diameter of 30 to 200 and have a gel partition coefficient, which is represented by Kay when using standard polyethylene oxide having a weight average molecular weight of $1.5 \times 10^5$ Da and using pure water as a mobile phase, of 0.15 to 0.6.

3. The porous cellulose gel according to claim 1, wherein the polysaccharides are dextran.

4. The porous cellulose gel according to claim 1, wherein the polysaccharides are pullulan.

5. The porous cellulose gel according to claim 1, wherein the porous cellulose particles are crosslinked cellulose particles having a water swelling degree of 5 to 20 ml/g.

6. A chromatography packing material, which is made by adding a ligand to the porous cellulose gel according to claim 1.

7. The packing material according to claim 6, wherein the ligand is a sulfone group.

8. The packing material according to claim 7, wherein the introduction amount of the ligand is 0.13 to 0.30 mmol/ml in terms of the ion exchange capacity.

9. The packing material according to claim 6, wherein the ligand is a sulfate group.

10. The packing material according to claim 9, wherein the introduction amount of the ligand is 5000 to 60000 ppm in terms of the sulfur content.

11. The packing material according to claim 6, which is used in purification of immunoglobulin.

12. The packing material according to claim 11, wherein the adsorption amount of immunoglobulin is 150 to 250 mg/ml.

13. The packing material according to claim 12, wherein the adsorption amount of immunoglobulin is 190 to 250 mg/ml.

14. A method for producing a chromatography packing material, comprising the step of adding a ligand to a porous cellulose gel, which is made by adding polysaccharides having a limiting viscosity of 0.21 to 0.90 dL/g to porous cellulose particles, the dry eight per unit volume of the porous cellulose gel being 1.06 to 1.40 times the dry weight per unit volume of the porous cellulose particles.

15. The method according to claim 14, wherein the porous cellulose particles have a particle diameter of 30 to 200 µm, and have a gel partition coefficient, which is represented by Kav when using standard polyethylene oxide having a weight average molecular weight of $1.5 \times 10^5$ Da and using pure water as a mobile phase, of 0.15 to 0.6.

16. The method according to claim 14, wherein the polysaccharides are dextran.

17. The method according to claim 14, wherein the polysaccharides are pullulan.

18. A method for producing an immunoglobulin preparation, comprising the steps of contacting a preparation comprising an immunoglobulin with the packing material according to claim 6 and separating and purifying the immunoglobulin.

* * * * *